(12) United States Patent
Osypka et al.

(10) Patent No.: US 9,572,957 B2
(45) Date of Patent: Feb. 21, 2017

(54) STEERABLE MEDICAL DEVICES AND STEERING ASSEMBLIES

(71) Applicant: Oscor Inc., Palm Harbor, FL (US)

(72) Inventors: Thomas P. Osypka, Palm Harbor, FL (US); Jeff J. Drum, Palm Harbor, FL (US); Michael J. Gelineau, Odessa, FL (US); Brett Garlock, Palm Harbor, FL (US); Andrew Enerson, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 112 days.

(21) Appl. No.: 14/639,448

(22) Filed: Mar. 5, 2015

(65) Prior Publication Data

US 2015/0258307 A1    Sep. 17, 2015

Related U.S. Application Data

(60) Provisional application No. 61/954,101, filed on Mar. 17, 2014.

(51) Int. Cl.
*A61M 25/00*  (2006.01)
*A61M 25/01*  (2006.01)

(52) U.S. Cl.
CPC ...... *A61M 25/0136* (2013.01); *A61M 25/0108* (2013.01); *A61M 25/0147* (2013.01)

(58) Field of Classification Search
CPC ....................... A61M 25/0136; A61M 25/0147
USPC ........................................................ 604/528
See application file for complete search history.

(56) References Cited

U.S. PATENT DOCUMENTS

| | | | |
|---|---|---|---|
| 2005/0197623 A1* | 9/2005 | Leeflang | A61M 25/0144 604/95.04 |
| 2007/0260223 A1* | 11/2007 | Scheibe | A61M 25/0136 604/528 |

* cited by examiner

*Primary Examiner* — Deanna K Hall
(74) *Attorney, Agent, or Firm* — Locke Lord LLP; Scott D. Wofsy; Daniel J. Fiorello

(57) ABSTRACT

A surgical apparatus includes an elongated handle assembly having opposed proximal and distal end portions and an interior cavity. An elongated sheath extends from the proximal end of the handle assembly, through the interior cavity of the handle assembly and out from the distal end portion of the handle assembly. The sheath includes an interior lumen extending therethrough and a distal end portion of the sheath is deflectable. The surgical apparatus includes a steering mechanism operatively associated with the handle assembly for controlling deflection of the deflectable distal end portion of the sheath. The steering mechanism includes a pull wire retraction assembly configured to selectively retract a pull wire to deflect the distal end portion of the sheath and a telescoping tube system for straightly guiding the pull wire as the pull wire retraction assembly moves within the interior cavity of the handle assembly.

6 Claims, 5 Drawing Sheets

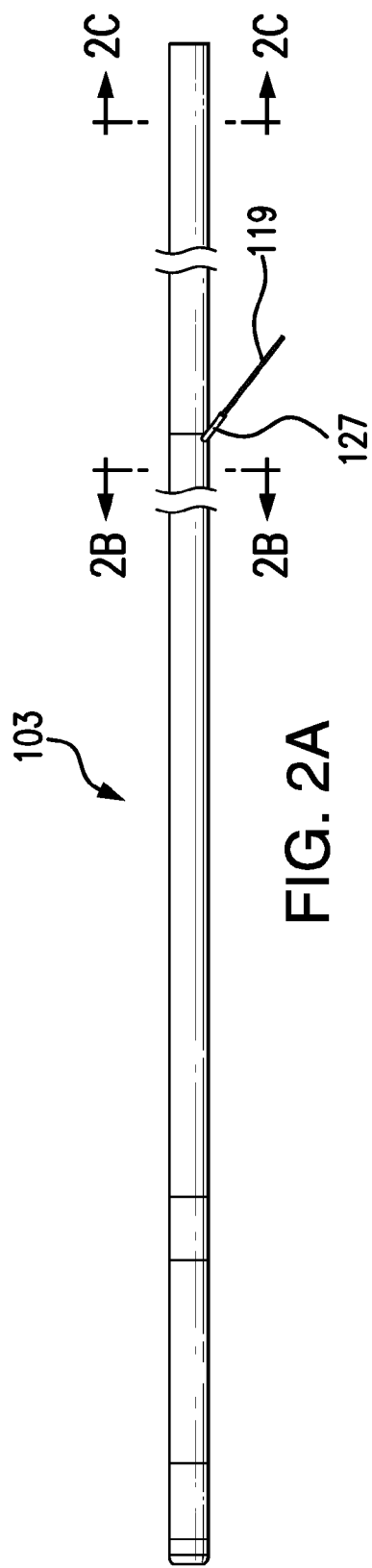
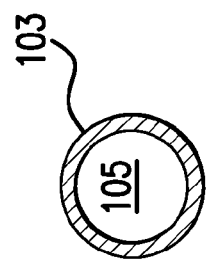
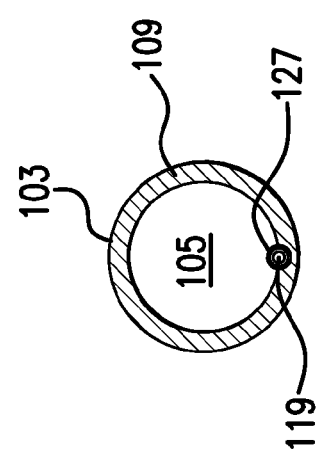

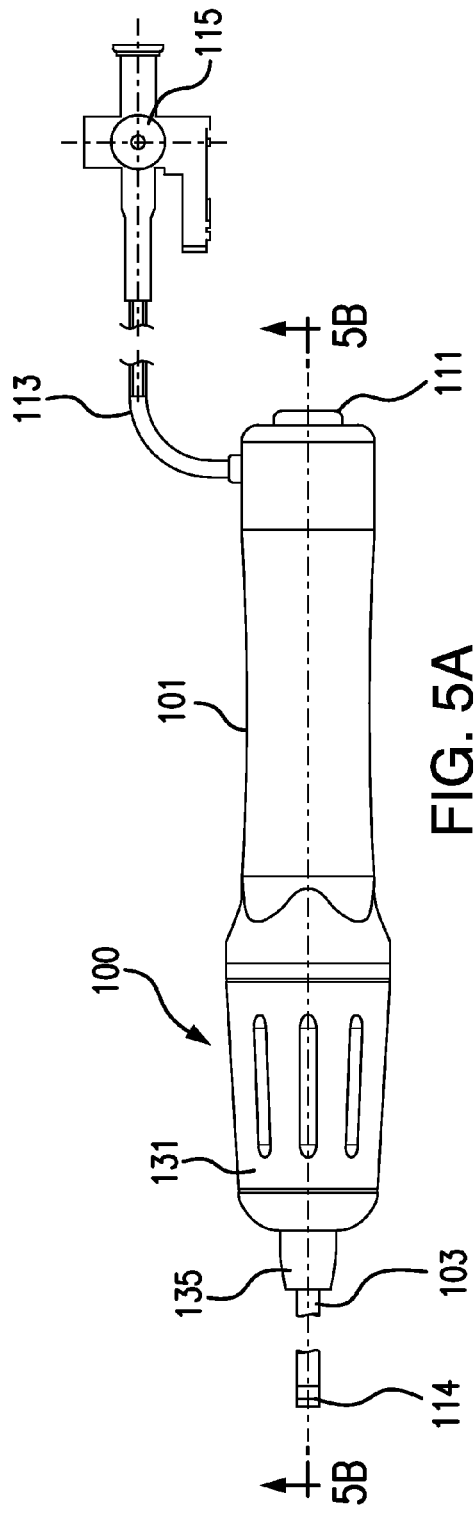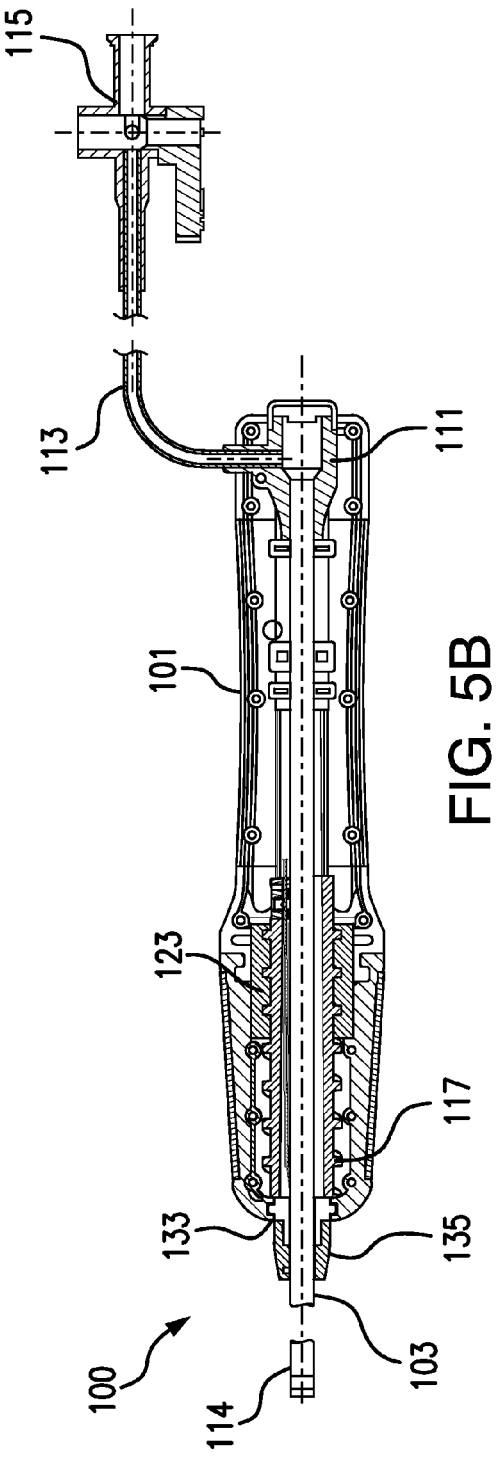
FIG. 5A
FIG. 5B

STEERABLE MEDICAL DEVICES AND STEERING ASSEMBLIES

CROSS-REFERENCE TO RELATED APPLICATIONS

This application claims the benefit of and priority to U.S. Provisional Application No. 61/954,101, filed Mar. 17, 2014, the content of which is incorporated by reference herein in its entirety.

BACKGROUND OF THE INVENTION

1. Field of the Invention

This disclosure is directed to intravascular surgery, more particularly, to a sheath or catheter having a deflectable distal end portion that is controlled by a unidirectional steering handle.

2. Description of Related Art

Guiding catheters ("sheaths") are commonly used to introduce balloon catheters and stents into the vascular system (e.g., for percutaneous transvascular coronary angioplasty), to introduce cardiac pacing leads into the coronary sinus (e.g., for left ventricular pacing and cardiac resynchronization procedures), to introduce drugs into the human body, and/or to introduce radiofrequency ablation catheters into the left atrium (e.g., for treatment of atrial fibrillation) into the renal artery for renal denervation procedures.

Guiding sheaths typically come in French sizes ranging from 4F all the way to 12F, and in some cases even 18F. Sheaths generally include an inner lumen that extends from the proximal portion of the device to the distal tip section of the device. The inner lumen often has a polytetrafluoroethylene (PTFE) liner to make the insertion of a device therethrough as easy and as smooth as possible.

Intravascular sheaths with a deflectable distal portions have the advantage of being introduced into a blood vessel in a straight condition, and thereafter the device can be remotely steered into a desired location by deflection the distal tip of the sheath, even though torturous and tight vessels. A common problem associated with traditional deflectable catheter sheaths is that, once they have been deflected, they do not readily return to a completely straight position for removal from the target location at the end of a procedure. This can inhibits the sheath from being easily retracted or withdrawn through the blood vessel or advanced into other desired locations within the vasculature of the patient.

Additionally, a wire inside the steering assembly that is connected to the distal end of the sheath can become twisted or create an undesirable force on the proximal end of the sheath where the wire enters the sheath when the device is operated between deflected and non-deflected states. Such undesirable forces and degrade the wire and/or the sheath, potentially compromising the functionality thereof.

While traditional guiding sheaths have been satisfactory for their intended purpose, a need exists for improved guiding catheters and steering assemblies. This disclosure provides solutions for these needs.

SUMMARY OF THE INVENTION

At least one aspect of this disclosure includes a surgical apparatus having an elongated handle assembly having opposed proximal and distal end portions and an interior cavity. An elongated sheath extends from the proximal end of the handle assembly, through the interior cavity of the handle assembly and out from the distal end portion of the handle assembly. The sheath includes an interior lumen extending therethrough and a distal end portion of the sheath is deflectable.

The surgical apparatus includes a steering mechanism operatively associated with the handle assembly for controlling deflection of the deflectable distal end portion of the sheath. The steering mechanism includes a pull wire extending from the distal end of the sheath into the interior cavity of the handle assembly, a pull wire retraction assembly within the interior cavity of the handle assembly and configured to selectively retract a pull wire to deflect the distal end portion of the sheath, and a telescoping tube system for straightly guiding the pull wire as the pull wire retraction assembly moves within the interior cavity of the handle assembly through movement of the pull wire retraction assembly.

The pull wire retraction assembly can include a worm gear mounted for reciprocal longitudinal movement within the interior cavity of the handle assembly relative to the handle assembly. The steering mechanism can include a rotatable drive nut meshed with the worm gear for effectuating the reciprocal longitudinal movement thereof. The pull wire can extend from the worm gear, through a wire hole in an outer wall of the sheath, to the deflectable distal end portion of the sheath.

The telescoping tube system can include a first tube affixed at a distal end to the sheath and a second tube secured to a proximal end portion of the worm gear. The second tube can be secured to the proximal end portion of the worm gear by a set screw. The set screw can crimp the pull wire within the second tube of the telescoping tube set.

The first tube can be affixed to the sheath at an angle relative to the sheath. The second tube can include a smaller diameter than the first tube. In certain embodiments, the first tube includes a smaller diameter than the second tube.

The first tube and the second tube can be directly slidably engaged with each other. The first tube can end at the distal end thereof proximal to the wire hole such that the pull wire exits the first tube proximal of the wire hole. The pull wire can exit the first tube at an angle less than about 45 degrees.

The handle assembly can include a rotatable torque handle directly connected to the drive nut in the interior cavity of the handle assembly. The handle assembly can include a hemostatic valve seated at a proximal end thereof to seal a proximal opening of the interior lumen of the sheath.

The handle assembly can include a side port tube in fluid communication with the interior lumen of the sheath. The side port tube can include a manual valve. In certain embodiments, the distal end portion of the sheath includes a radiopaque marker.

A method can include attaching a telescoping tube system to a pull wire retraction assembly and a sheath of a steerable medical device and disposing a wire within the telescoping tube system. Attaching the telescoping tube can include setting a set screw to clamp a portion of the telescoping tube system to the pull wire retraction assembly.

These and other features of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the embodiments of this disclosure without undue experimentation, preferred embodiments thereof will be described in detail herein below with reference to certain figures, wherein:

FIG. 2A is a side elevational view of the sheath of the surgical device of FIG. 1;

FIG. 2B is a cross-section view of a distal portion of the sheath of FIG. 2A;

FIG. 2C is a cross-section view of a proximal portion of the sheath of FIG. 2A;

FIG. 5A is an enlarged view of the handle assembly of the surgical device of FIG. 1;

FIG. 5B is a cross-sectional view of the handle assembly of FIG. 5A; and

DETAILED DESCRIPTION OF PREFERRED EMBODIMENTS

Figure 1:
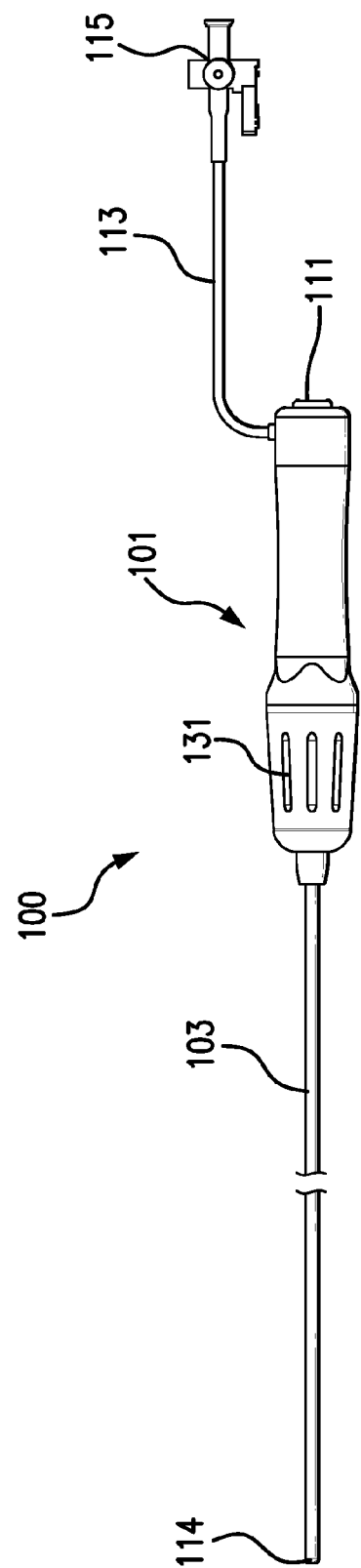
FIG. 1 is a top plan view of an embodiment of a surgical device constructed in accordance with the present disclosure, which includes a handle assembly and an elongated sheath with a deflectable distal end portion that is shown in a straightened condition.

Referring now to the drawings wherein like reference numerals identify similar structural elements or features of the embodiments of this disclosure, an embodiment of a surgical apparatus 100 constructed in accordance with this disclosure is shown in FIG. 1. Other features of the surgical apparatus 100 are shown in FIGS. 2A-5C.

Referring to FIG. 1, the surgical apparatus 100 includes an elongated handle assembly 101 having opposed proximal and distal end portions. The handle assembly 101 defines an interior cavity (e.g., see FIG. 5B). An elongated sheath 103 extends from the proximal end of the handle assembly 101, through the interior cavity of the handle assembly 101 and out from the distal end portion of the handle assembly 101.

Referring to FIGS. 2A-4, the sheath 103 includes an interior lumen 105 extending therethrough. A distal end portion of the sheath 103 is configured to be deflectable. For example, a suitable distal portion of the sheath 103 can include a reduced thickness relative to a proximal portion. The deflectable distal end portion of the sheath 103 can be adapted and configured for unidirectional deflection to any suitable angle relative to the straightened condition in which it is aligned with the normal longitudinal axis of the sheath 103 (e.g., in the range of between about 90° and about 180°).

Figure 4:
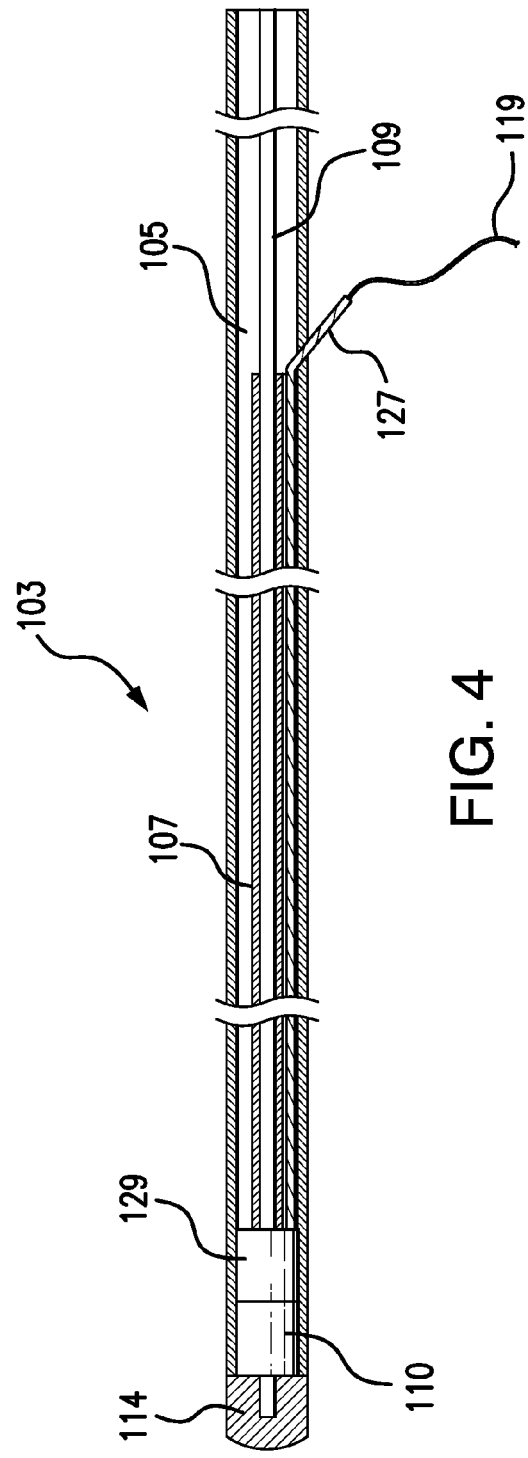
FIG. 4 is a cross-sectional view of the sheath of the surgical device of FIG. 1, illustrating, among other aspects of the sheath, the pull wire extending through the wall of the sheath to the distal end portion of the sheath.

The sheath 103 can be formed from polymer tubing and/or any other suitable material. Referring to FIG. 4, the sheath 103 can be reinforced with braiding 107 on and/or within the sheath. Any other suitable structural feature is contemplated for reinforcement (e.g., a semi-rigid rod or liner 109 disposed within the inner lumen 105). As shown in FIG. 4, the distal end portion of the sheath 103 can include a radiopaque marker 110 and/or any other suitable positional marker for locating the distal end portion 114 in situ to enable the visual guidance of the sheath 103 using a suitable imaging system. The sheath 103 can also include a soft atraumatic tip portion 114 disposed on the distal end thereof. In some embodiments, the tip portion 114 can include one or more side holes (not shown) in fluid communication with the interior lumen 105 of the sheath 103.

Figure 5C:
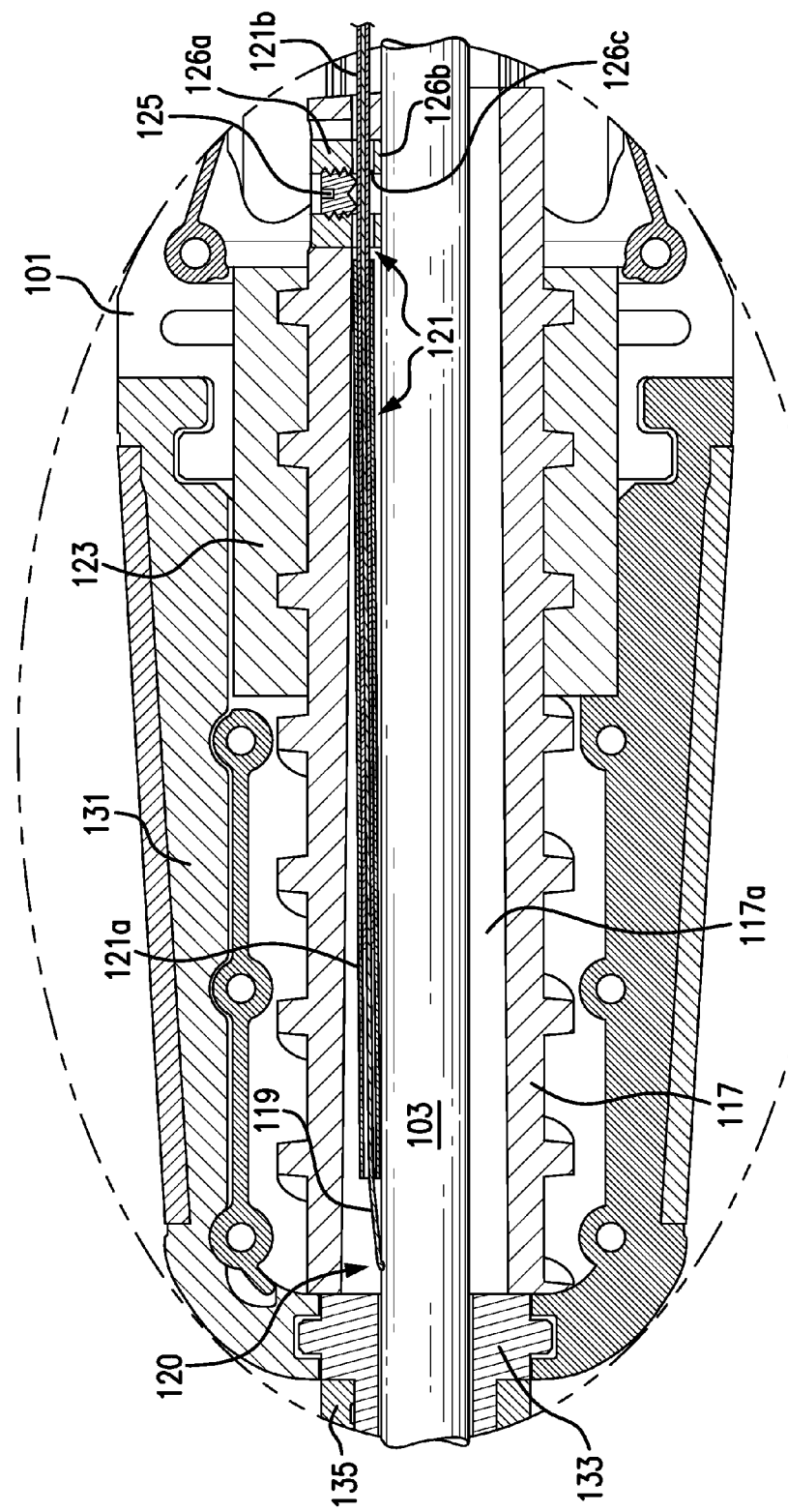
FIG. 5C is an enlarged localized view taken from FIG. 5B, showing the pull wire extending from the distal end of the second tube of the telescoping tube set which guides and maintains the pull wire in a straightened condition as the worm gear of the steering mechanism moves within the handle assembly in response to axial rotation of the drive nut.

Referring additionally to FIGS. 5B and 5C, the sheath can be supported as a distal end of the handle assembly 101 by a sheath support 133 and/or a strain relief portion 135. The sheath support 133 and/or strain relief portion 135 can be fixed to the sheath 103 in any suitable manner (e.g., adhesive).

Figure 3:
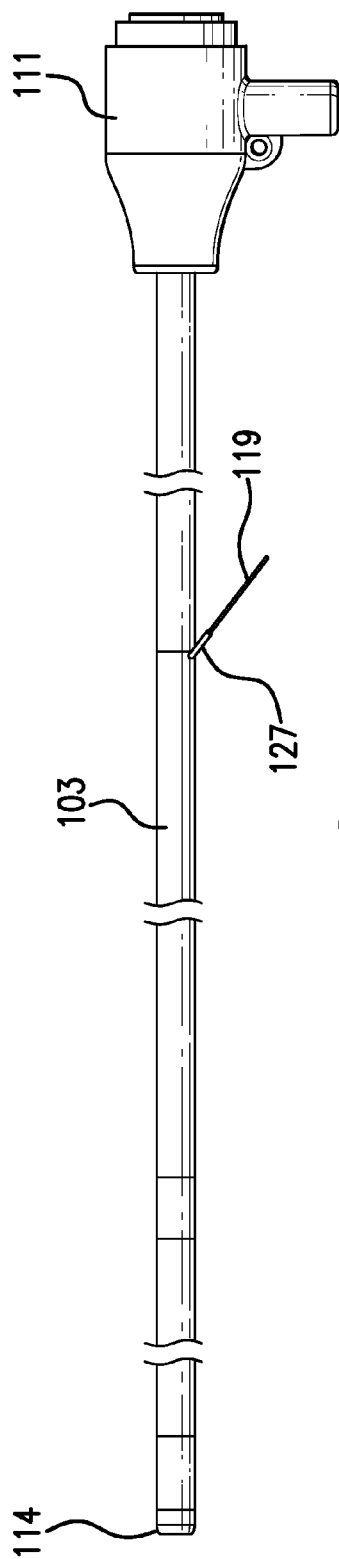
FIG. 3 is a side elevational view of the sheath of the surgical device of FIG. 1, illustrating a hemostatic seal operatively connected thereto.

Referring to FIG. 3, the sheath 103 can be operatively connected to a hemostatic valve 111. Referring to FIGS. 5A and 5B, the hemostatic valve 111 can be seated at a proximal end of the handle assembly 101 to seal a proximal opening of the interior lumen 105 of the sheath 103. The hemostatic valve 111 can be configured to facilitate the sealed introduction of a therapeutic device and/or any other suitable medical device (e.g., a dilator).

The handle assembly 101 can also include a side port tube 113 in fluid communication with the interior lumen 105 of the sheath 103 to enable irrigation or delivery of a medicament and/or other any other suitable fluid (e.g., dye) through the tip portion 114. The side port tube 113 can include a manually operated fluid control valve 115 such as, for example, a 3-way stopcock valve with a luer fitting and/or a similar valve. Any other suitable type of valve is contemplated herein.

Referring to FIGS. 5A-5C, the surgical apparatus 100 also includes a steering mechanism operatively associated with the handle assembly 101 for controlling deflection of the deflectable distal end portion of the sheath 103. The steering mechanism includes a pull wire retraction assembly (e.g., worm gear 117 as shown) configured to selectively retract a pull wire 119 to deflect the distal end portion of the sheath 103. While the steering mechanism is shown including only single pull wire 119 for unidirectional deflection, however, it is contemplated that multiple pull wires 119 can be used for any suitable type of deflection (e.g., bidirectional, multidirectional).

As shown, a worm gear 117 is mounted for reciprocal longitudinal movement within the interior cavity of the handle assembly 101 relative to the elongated sheath 103. The steering mechanism further includes an axially rotatable drive nut 123 meshed with the worm gear 117 for effectuating the reciprocal longitudinal movement of the worm gear 117. When the drive nut 123 is rotated, the worm gear 117 moves longitudinally in either the distal or proximal direction.

As shown in FIG. 5C, the worm gear 117 is advanced to a distal position such that the worm gear abuts the inner surface of the handle assembly 101 such that the worm gear 117 cannot be advanced further in the distal direction. This position can be associated with a straight condition of the sheath 103. The worm gear 117 can be advanced proximally by rotation of the drive nut 123 to pull the pull wire 119 and deflect the distal end of the sheath 103.

Referring to FIG. 5C, a telescoping tube system 121 can be operatively disposed within a core 117a of the worm gear 117 for straightly guiding the pull wire 119 as the worm gear 117 moves within the interior cavity of the handle assembly 101 in response to the axial rotation of the drive nut 123. The telescoping tube system 121 can include a first tube 121a that is affixed or otherwise connected to the sheath 103 within the core 117a of the worm gear 117. The first tube 121a can be fixed to the sheath 103 in any suitable manner (e.g., adhesives, bonding, latching, tying).

The telescoping tube system 121 can include a second tube 121b the can move relative to the first tube 121a. The second tube 121b can be secured to a proximal end portion of the worm gear 117. As shown, in certain embodiments, the second tube 121b can be releasably secured to the proximal end portion of the worm gear 117 by a set screw 125. The worm coil 117 can include a set screw receiving member 125a disposed in the worm coil 117. The set screw receiving member 126a can include one or more flanges 126b which define a channel 126c for the second tube 121b to pass therethrough. The flanges 126b allow for the second tube 121b to be clamped by the set screw 125 to the set screw receiving member 126a.

While it is shown that the second tube 121b can be selectively removable from the worm coil 117, it is contemplated that the second tube 121b could be permanently connected to the worm gear 117 in any suitable manner. Any other suitable type of connection is contemplated herein.

The first tube 121a and/or second tube 121b can be affixed to the sheath 103 at an angle relative to the sheath 103. However, it is contemplated that the tubes 121a, 121b can be parallel with the sheath 103. Also, as shown in this embodiment, the second tube 121b can include a smaller diameter than the first tube 121a. In certain embodiments, it is contemplated that the first tube 121a can have a smaller diameter than the second tube 121b. In this regard, the first tube 121a and the second tube 121b can be directly slidably engaged with each other to telescope when the worm gear 117 is moved longitudinally. While two straight tubes 121a, 121b are shown, it is contemplated that the telescoping system 121 can include any suitable number of tubes of any suitable shape (e.g. curved). It is also contemplated that the telescoping tube system 121 can be applied to devices with multiple pull wires 119 (e.g., a bidirectional or multidirectional steering mechanism).

The first tube 121a can end at the distal end thereof proximal to a pull wire hole 120 such that the pull wire 119 exits the first tube 121a proximal of the wire hole 120. The tubes 121a, 121b can be configured such that the pull wire 119 can exit the first tube 121a at any suitable angle relative to the sheath 103 (e.g., less than about 45 degrees, about 90 degrees).

In the depicted configuration, the pull wire 119 extends through the second tube 121b of the telescoping tube system 121, through the first tube 121a, out from the distal end of the first tube 121a, and into a pull wire hole 120 in the sheath 103. The pull wire 119 can be secured fixedly within the second tube 121b by the set screw 125 that secures the second tube 121b to the worm gear 117. In this regard, the set screw 121b can function to crimp the pull wire 119 at the proximal end of the second tube 121b.

As shown in FIGS. 2B, 4, and 5C, the pull wire 119 can run from the core 117a of worm gear 117, through an outer wall of the sheath 103, to the distal end portion of the sheath 103. Referring to FIG. 4, the pull wire 119 can pass through a composite tube 127 that extends through the sheath 103 along the inner lining of the outer wall of the sheath 103. As shown in FIG. 2B, it is contemplated that the composite tubing 127 can be at least partially encapsulated in the wall of the sheath 103.

Referring to FIG. 4, the pull wire 119 can be fixed to an anchor member 129 that is fixed to the distal end portion of the sheath 103. The anchor member 129 can be proximal of the radiopaque marker 110 or in any other suitable longitudinal position in the sheath 103.

Referring to FIGS. 1 and 5A-5C, the handle assembly 101 can include a rotatable torque handle 131 directly connected to the drive nut 123 in the interior cavity of the handle assembly 101. The torque handle 131 can be configured for gripping and rotation by a user to rotate the drive nut 123 and move the work coil 117. The torque handle 131 can be rotatably mounted around the sheath support 133 and a proximal portion of the handle assembly 101 as shown.

A method can include attaching a telescoping tube system 121 to a pull wire retraction assembly (e.g., worm coil 117) and a sheath 103 of a steerable medical device 100, and disposing a wire 119 within the telescoping tube system 121. Attaching the telescoping tube system 121 can include setting a set screw 125 to clamp a portion of the telescoping tube system 121 to the pull wire retraction assembly.

The telescoping tube systems 121 and methods as described above allow for the tubes 121a, 121b to slide relative to each other to maintain the pull wire 119 in a straight condition in all longitudinal positions of the worm coil 117. The orientation of the pull wire 119 relative to wire hole 120 can be maintained as well. Maintaining the straightness and position of the pull wire 119 can prevent the pull wire from tangling, twisting, and/or grinding on the sheath 103 and can provide a better and more controllable force translation to the distal end of the sheath 103.

Those skilled in the art should readily appreciate that the above described steering mechanism can be used or otherwise included in other types of steerable medical devices aside from the intravascular catheter sheath illustrated and described herein. For example, the steering mechanism could be employed with any type of steerable catheter or even with steerable endoscopes or the like.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:
1. A surgical apparatus comprising:
  a) an elongated handle assembly having opposed proximal and distal end portions and an interior cavity;
  b) an elongated sheath extending from the proximal end portion of the handle assembly, through the interior cavity of the handle assembly and out from the distal end portion of the handle assembly, the sheath having an interior lumen extending therethrough, wherein a distal end portion of the sheath is deflectable; and
  c) a steering mechanism operatively associated with the handle assembly for controlling deflection of the deflectable distal end portion of the sheath, the steering mechanism including:
    i) a pull wire extending from the distal end portion of the sheath into the interior cavity of the handle assembly;
    ii) a pull wire retraction assembly supported within the interior cavity of the handle assembly and configured to selectively retract the pull wire to deflect the distal end portion of the sheath, the pull wire retraction assembly including a worm gear mounted for reciprocal longitudinal movement within the interior cavity of the handle assembly, and an axially rotatable drive nut meshed with the worm gear for effectuating the reciprocal longitudinal movement thereof; and iii) a telescoping tube system for straightly guiding the pull wire as the pull wire retraction assembly moves within the interior cavity of the handle assembly, the telescoping tube system including a longitudinally straight, unbent stationary outer tube affixed at a distal end thereof to the sheath and a longitudinally straight telescoping inner tube disposed partially within the unbent stationary outer tube and secured at a proximal end thereof to the worm gear within a set screw anchor by a set screw that crimps the proximal end of the telescoping inner tube that extends through the set screw anchor so as to secure the pull wire within the telescoping inner tube member, wherein the pull wire extends from the telescoping inner tube member, through an outer wall of the sheath, to an anchor member in the deflectable distal end portion of the sheath, passing through a composite tube that extends through the sheath along an inner lining of the outer wall of the sheath.

2. The apparatus of claim 1, wherein the handle assembly includes a rotatable torque handle directly connected to the drive nut in the interior cavity of the handle assembly.

3. The apparatus of claim 1, wherein the handle assembly includes a hemostatic valve seated at a proximal end thereof to seal a proximal opening of the interior lumen of the sheath.

4. The apparatus of claim 1, wherein the handle assembly includes a side port tube in fluid communication with the interior lumen of the sheath.

5. The apparatus of claim 4, wherein the side port tube includes a manual valve.

6. The apparatus of claim 1, wherein the distal end portion of the sheath includes a radiopaque marker distal to the anchor member.

* * * * *